(12) United States Patent
Merida

(10) Patent No.: US 10,335,435 B2
(45) Date of Patent: Jul. 2, 2019

(54) METHOD FOR ENDOSCOPICALLY DELIVERING STEM CELLS TO THE BRAIN USING AN INTRANASAL, INJECTABLE APPROACH

(71) Applicant: Marco Merida, McLean, VA (US)

(72) Inventor: Marco Merida, McLean, VA (US)

( * ) Notice: Subject to any disclaimer, the term of this patent is extended or adjusted under 35 U.S.C. 154(b) by 480 days.

(21) Appl. No.: 15/159,073

(22) Filed: May 19, 2016

(65) Prior Publication Data

US 2016/0339059 A1 Nov. 24, 2016

Related U.S. Application Data

(60) Provisional application No. 62/165,240, filed on May 22, 2015.

(51) Int. Cl.
| | | |
|---|---|---|
| A61K 35/28 | (2015.01) | |
| A61K 9/00 | (2006.01) | |
| A61B 1/233 | (2006.01) | |

(52) U.S. Cl.
CPC ............ *A61K 35/28* (2013.01); *A61K 9/0019* (2013.01); *A61K 9/0085* (2013.01); *A61B 1/233* (2013.01); *A61K 9/0043* (2013.01); *A61M 2210/0681* (2013.01)

(58) Field of Classification Search
CPC ...... A61B 1/233; A61K 35/28; A61K 9/0019; A61K 9/0043; A61K 9/0085; A61M 2210/0681

See application file for complete search history.

(56) References Cited

U.S. PATENT DOCUMENTS

(56) References Cited

| | | | |
|---|---|---|---|
| 5,620,446 | A | 4/1997 | McNamara et al. |
| 5,669,903 | A | 9/1997 | O'Donnell |
| 5,817,073 | A | 10/1998 | Krespi |
| 6,410,046 | B1 | 6/2002 | Lerner |
| 7,033,598 | B2 | 4/2006 | Lerner |
| 8,230,867 | B2 | 7/2012 | Mark |
| 8,241,266 | B2 | 8/2012 | Keith et al. |
| 8,283,160 | B2 | 10/2012 | Frey, II et al. |
| 8,518,390 | B2 | 8/2013 | Kramer et al. |
| 8,583,229 | B2 | 11/2013 | Rezai et al. |
| 8,609,088 | B2 | 12/2013 | Wolf et al. |
| 8,666,479 | B2 | 3/2014 | Berndt |
| 8,771,303 | B1 | 7/2014 | Jurbala |
| 2001/0038836 | A1 | 11/2001 | During et al. |
| 2001/0043915 | A1 | 11/2001 | Frey, II |
| 2001/0046489 | A1 | 11/2001 | Habener et al. |
| 2002/0068080 | A1 | 6/2002 | Lerner |
| 2003/0054035 | A1 | 3/2003 | Chu et al. |
| 2003/0133877 | A1* | 7/2003 | Levin .................. A61K 9/0043 424/45 |
| 2003/0165434 | A1 | 9/2003 | Reinhard et al. |
| 2003/0229025 | A1 | 12/2003 | Xiao et al. |
| 2005/0032209 | A1 | 2/2005 | Messina et al. |
| 2007/0269385 | A1 | 11/2007 | Yun et al. |
| 2008/0260699 | A1 | 10/2008 | Parman |
| 2009/0068155 | A1 | 3/2009 | Frey, II et al. |
| 2009/0270806 | A1 | 10/2009 | Macaulay et al. |
| 2010/0158943 | A1 | 6/2010 | Vajdy et al. |
| 2010/0228227 | A1 | 9/2010 | Krespi et al. |
| 2011/0040144 | A1 | 2/2011 | Jackson |
| 2011/0152974 | A1 | 6/2011 | Rezai et al. |
| 2011/0177170 | A1 | 7/2011 | Kryukhovetskiy et al. |
| 2012/0014921 | A1 | 1/2012 | Kramer et al. |
| 2013/0028874 | A1 | 1/2013 | Frey, II et al. |
| 2013/0066271 | A1 | 3/2013 | West |
| 2013/0336938 | A1* | 12/2013 | Bloch .................... A61K 35/39 424/93.21 |
| 2014/0012076 | A1 | 1/2014 | Mirza et al. |
| 2015/0045822 | A1 | 2/2015 | Mirza et al. |

FOREIGN PATENT DOCUMENTS

WO 2013006076 A1 1/2013

OTHER PUBLICATIONS

Djupesland, et al., "The nasal approach to delivering treatment for brain diseases: an anatomic, physiologic, and delivery technology overview", Therapeutic Delivery (2014) 5(6), pp. 709-731.
Sahin-Yilmaz et al., "Anatomy and Physiology of the Upper Airway", Proc Am thorac Soc, vol. 8, (2011), pp. 31-39. Danielyan et al., "Therapeutic efficacy of intranasally delivered mesenchymal stem cells in a rat model of Parkinson disease", Rejuvenation Res., Feb. 2011, 2 pages.
Chapman et al., "Intranasal Treatment of Central Nervous System Dysfunction in Humans", Pharm. Res (2013), pp. 2475-2484.
Gomez et al., "Intranasal treatment of neurodegenerative diseases and stroke", Frontier in Bioscience S4, Jan. 1, 2012, 36 pages.
KurzweilAI/Accelerating Intelligence.News "Missing link found between brain, immune system", Jun. 2, 2015, 3 pages.
Balyasnikova et al., "Intranasal Delivery of Mesenchymal Stem Cells Significantly Extends Survival of Irradiated Mice with Experimental Brain Tumors", Molecular Therapy (2014), 20 pages.
J. Barney, "Researchers Find Textbook-Altering Link Between Brain, Immune System", UVA Today, Jun. 1, 2015, 3 pages.
Therapeutic Intranasal Drug Delivery, "Anatomy and Physiology of the nose: Key points relating to nasal drug delivery" retrieved from the internet May 19, 2016, 5 pages.

(Continued)

*Primary Examiner* — Brandy S Lee
(74) *Attorney, Agent, or Firm* — Edell, Shapiro & Finnan, LLC

(57) ABSTRACT

A method is disclosed for delivery of stem cells to the central nervous system, particularly the brain, using an intranasal, injectable approach for the treatment of neurological deficits. The injectable approach employs a syringe to inject a stem cell solution or suspension into mucosal tissue of the nose using endoscopy. The approach provides direct endoscopic visual access to mucosal and sub-mucosal tissue selected for injection and the depth of placement of stem cells within the selected mucosal and sub-mucosal tissue. Placement of stem cells solely within the mucosal and sub-mucosal tissue assures survival of the stem cells and improves the likelihood the stem cells will reach specific sites of damage within the brain. This endoscopic intranasal approach is useful as therapy for patients who may benefit (Continued)

from cellular therapy as a result of stroke, brain trauma, and neurodegenerative conditions.

11 Claims, No Drawings

(56) References Cited

OTHER PUBLICATIONS

Abbott NJ, "Blood-brain barrier structure and function and the challenges for CNS drug delivery", J Inherit Metab Dis., May 2013, 1 page.

Merkus et al., "Can nasal drug delivery bypass the blood-brain barrier?: questioning the direct transport theory", Drugs RD, 2007, 1 page.

* cited by examiner

METHOD FOR ENDOSCOPICALLY DELIVERING STEM CELLS TO THE BRAIN USING AN INTRANASAL, INJECTABLE APPROACH

CROSS REFERENCE TO RELATED APPLICATIONS

The present application is a non-provisional application based on and claiming priority from U.S. Provisional Application No. 62/165,240, entitled "Method For Endoscopically Delivering Stem Cells To The Brain Using An Intranasal, Injectable Approach" and filed May 22, 2015, the disclosure which is hereby incorporated herein by reference in its entirety.

FIELD OF THE INVENTION

The present invention generally relates to a method for delivering stem cells to the brain of a human to treat a damaged, degenerating and/or injured central nervous system. More particularly, the present invention relates to a method of administering a stem cell solution or suspension into mucosal tissue of the nose via an intranasal (IN) approach using endoscopy to treat stroke, brain trauma, neurodegenerative conditions such as Alzheimer's and Parkinson's diseases, and other diseases and trauma that result in a damaged, degenerating and/or injured central nervous system.

BACKGROUND OF THE INVENTION

Diseases, disorders, and injuries of the central nervous system are associated with loss and/or dysfunction of neurons and/or glia. These diseases, disorders, and injuries range from simple monogenetic diseases to complex acquired disorders and trauma. These diseases, disorders, and injuries include, but are not limited to, stroke, Huntington's disease, Alzheimer's disease, Parkinson's disease, amyotrophic lateral sclerosis, brain trauma, spinal cord injury, myelin disorders, immune and autoimmune disorders, metabolic and storage diseases including all of the leukodystrophies and lysosomal storage diseases, and other degenerative, oncological, metabolic, or senescence-related diseases and disorders of the central nervous system (CNS). These neurodegenerative diseases, as well as the neurological damage associated with these conditions, are very difficult to treat and were thought to be irreversible because of the inability of neurons and other cells of the nervous system to grow in the adult body.

However, the recent advent of stem cell-based therapy for tissue repair and regeneration provides promising treatments for a number of neurodegenerative pathologies and other neurological disorders. Accumulating evidence suggests that delivery of therapeutic stem cells to the brain of a human can have a potential beneficial effect in treating many diseases, disorders, and injuries with central nervous system involvement since stem cells are capable of self-renewal and differentiation to generate a variety of mature neural cell lineages. These diseases, disorders, and injuries include, but are not limited to, stroke, brain trauma and neurodegenerative conditions such as Alzheimer's, Parkinson's and Huntington's diseases.

However, there are many hurdles preventing therapeutic agents as well as therapeutic stem cells, from reaching a diseased brain. For instance, systemic delivery of therapeutic agents to the CNS is ineffective for most small molecules and nearly all large molecules. The main impediment in most cases is the blood-brain barrier (BBB). Necessary for protection against bacterial infections, the BBB prevents most foreign substances, including potential therapeutic agents and stem cells, from entering the brain from capillaries.

Early conventional approaches or strategies to bypassing (circumventing) the blood brain barrier using IV infusion via intrathecal or intracranial routes have not yielded unanimous or encouraging reproducible results. In addition, each of these approaches included limitations, such as the inherent risks associated with an invasive surgical procedure, and potentially undesirable side effects associated with the systemic administration of therapeutic agents. Similarly, the blood brain barrier has presented a significant obstacle to efficient and effective delivery of stem cells to the brain using noninvasive techniques such as suspension solutions or ointment delivered by intranasal sprays or direct intranasal application of drops or ointment to nasal tissue, e.g., by swab or pledget, because of the unpredictable effect of cilia activity, moisture and humidity and air flow currents that occur normally in the nose. Moreover, these delivery approaches have proven to be suboptimal in reaching target sites beyond the nasal valve, e.g., damaged regions within the brain and/or CNS, due to their inability to reach the olfactory region of the brain as well as their very limited ability to deposit therapeutic stems cells within the damaged regions of the brain and/or CNS. As a result of these factors, the dose and potential absorption of the therapeutic stem cells is presently unpredictable.

Other prior approaches to bypassing the BBB have attempted intranasal injection of stem cell solutions using a nasal speculum and different light sources by inserting a needle into the periosteum or subperichondrial regions of non-specific areas of the nose. However, these approaches have proven to be unsatisfactory because of the lack of non-specificity of the region chosen for injection and the avascular nature of the location where the cells are deposited. In addition, the use of routine vasoconstrictors during surgery, for example, oxymetazoline, phenylephrine or cocaine, has further hampered the success of this approach. Nonetheless, accumulating evidence suggests that IN delivery of stem cells may be a viable approach for treatment of CNS pathology since complications associated with intravascular delivery, such as obstruction of the BBB, pulmonary embolism and infarctions, could also be avoided using the approach.

Therefore, since none of the methods discussed above has resulted in a combination of high efficiency and low side effects delivery of potential therapeutics (including stem cells) to the brain and/or CNS, there still exists a need for a better method to optimize or enhance delivery of therapeutics, particularly therapeutic stem cells, to the tissues and cells of the brain and/or CNS.

SUMMARY OF THE INVENTION

Accordingly, it is an object of the present invention to provide a method for intranasal delivery of stem cells to the brain in therapeutic concentrations to treat a damaged, degenerating and/or injured central nervous system.

It is another object of the present invention to provide an endoscopic procedure for intranasal delivery of stem cells to the brain in therapeutic concentrations to treat a damaged, degenerating and/or injured central nervous system.

It is a further object of the present invention to provide a minimally invasive method for intranasal delivery of stem cells to the brain which provides a direct visual approach to permit a surgeon to see endoscopically where the stem cells are to be delivered.

Still another object of the present invention is to provide an endoscopic method for intranasal delivery of stem cells which provides a direct visual approach to permit a surgeon to see the mucosal and sub-mucosal tissue of the nose where the stem cells are to be delivered.

Yet another object of the present invention is to provide an endoscopic procedure for intranasal delivery of stem cells to the brain which is not subject to deleterious physical factors such as air current drying effects, mucosal production, humidity, and diversionary effects of nasal cilia which can occur when stem cells are delivered via suspension solutions or ointments.

In one aspect of the present invention, the minimally invasive endoscopic procedure is performed under local anesthesia, or local anesthesia with sedation, or general anesthesia, depending on the patient's wishes and/or the surgeon's preference. The only requirement is that no nasal constrictor agent should be placed topically or injected into the nasal cavity or surgical sites to be used.

In another aspect of the present invention, the endoscopic procedure for intranasal delivery of stem cells to the brain differs from all prior intranasal stem cell procedures in that it is the first to establish a direct visual approach; that is, it permits the surgeon to directly see endoscopically where the stem cells are to be delivered to mucosal and sub-mucosal tissue of the nose.

The above mentioned and other objects, features and advantages of the present invention, as well as the manner of attaining them, will become better understood upon consideration of the following definitions and descriptions of specific embodiments thereof. While these descriptions go into specific details of the invention, it should be understood that variations may and do exist and would be apparent to those skilled in the art based on the descriptions herein.

DETAILED DESCRIPTION OF THE INVENTION

The delivery method of the present invention preferentially provides for intranasal (IN) delivery of stem cells for treatment of neurological deficits to specific sites of damage within the brain of mammals, especially the brain of humans. The intranasal approach of this invention preferably uses intranasal endoscopy to directly administer cells to the brain of a human and is useful as therapy for patients with neurological deficit and those in need of neural therapy such as patients with, but not limited to, stroke, traumatic injuries, neurodegenerative conditions such as Alzheimer's, Parkinson's and Huntington's diseases, or other cerebral damage or diseases of the brain. Thus, this minimally invasive IN method for delivering therapeutic stem cells to the brain is not only desirable and safe, but is efficient and effective.

The stem cells delivered to the brain by the endoscopic intranasal delivery approach of this invention may, for example, be stem cells of restricted (i.e., multipotent) or unlimited (i.e., totipotent or pluripotent) potential. However, the stem cells may also be modified prior to delivery. For instance, specific genes in stem cells may be manipulated to increase differentiation of specific neuronal subtypes, e.g., dopaminergic neurons. Alternatively, cells may be manipulated by chemical or other suitable proliferative or differentiation agents or by generic modification.

The delivery method of the present invention preferably utilizes an endoscopic device to deliver therapeutic agent (i.e., therapeutic stem cells) to selected mucosal tissue sites within the nasal cavity of the nose. The endoscopic device may be an endoscope containing an optical or visual system, as well as a light source, that allows a surgeon to see directly into the nasal cavity. The endoscope may further include a needle and a needle port or channel. Passing the needle through the port (channel) of the endoscope permits the needle to enter into the nasal cavity and be accurately positioned for injection of stem cells into mucosal and submucosal tissue of a selected site within the cavity. Endoscopes which may be suitable for intranasal delivery of stem cells to mucosal tissue within the nasal cavity of the nose are shown and described, for example, in U.S. Patent Publication No. 2011/0040144 (Jackson) and U.S. Pat. No. 5,817,073 (Krespi); the disclosures in which are incorporated herein by reference in their entireties.

However, one skilled in the art should appreciate that the intranasal delivery method of the present invention does not require the needle to be unitary with the endoscope. To the contrary, a needle and syringe that is separate and distinct from the endoscope may be passed into the nasal cavity in another way and, thereafter, accurately positioned for injection of stem cells into mucosal and sub-mucosal tissue by endoscopic guidance (imaging). Nevertheless, the use of an endoscope which includes the needle is preferred over other intranasal approaches since it provides direct access to mucosal tissue without otherwise more invasive procedures being performed. Moreover, once such access is provided, the method of the present invention may be performed by injection by a needle into the mucosal and sub-mucosal tissue area at various specific sites within the nasal cavity having an abundance of neurovascular components.

The thickness of the mucosa within the nasal cavity of the nose can vary depending on anatomy, but is typically within the range from about 0.1 to about 5.0 mm. Needless to say, accurate positioning of the needle within the mucosal area (i.e., the mucosa and sub-mucosa tissue) of a selected site in the nasal cavity is critical. As mentioned previously, the use of endoscopic imaging is an extremely important aspect of the present invention because it enables a surgeon to precisely inject stem cells (or other injectables) directly into the mucosal and sub-mucosal tissue which is rich in neurovascular components that promote absorption, transportation, and by-passing of the blood-brain barrier (BBB).

Prior to the intranasal endoscopic imaging approach of the present invention, surgeons would typically attempt intranasal injection of therapeutic agents, such as stems cells, using a nasal speculum and a light. Specifically, a surgeon would blindly insert a needle through the mucosa and into the periosteum until the needle hit bone. Upon hitting bone, the surgeon would inject the stem cells into the periosteum or perichondrium area adjacent the bone. However, periosteum and perichondrium regions are avascular areas, i.e., areas having little or no blood supply. Thus, if stem cells were to be deposited into these areas they would die for lack of a sufficient blood supply.

In one embodiment of the present invention, the intranasal delivery procedure includes the following steps:

(1) A patient (previously prepped and draped in a sterile fashion) is placed in a supine position;

(2) Approximately one hour prior to the start of the procedure, the patient receives an appropriate antibiotic intravenously to fight off any possible pathogens that might be detrimental during nasal or paranasal surgery, however, the antibiotic must be compatible with any medications being taken by the patient and with any patient allergies;

(3) The intranasal delivery procedure may be accompanied by intravenous (IV) administration or topical placement of any drug enhancers that would transiently open the blood-brain barrier and improve permeability of the stem cells through the BBB such as, for example, Mannitol; and (4) Thereafter, a surgeon (appropriately prepared in sterile fashion to perform the surgery) using standard endoscopic equipment to visualize the specific area of the nasal cavity that needs to be assessed, delivers therapeutic stem cells in a liquid solution (e.g., saline) or other physical suspension via a syringe and needle exclusively to the mucosal and sub-mucosal tissue at the site or sites selected for injection.

In a further embodiment of the present invention, the placement as well as the order of placement of the therapeutic stem cells (or other injectables) in the mucosa of the nasal cavity via intranasal injection depends on the surgeon's preference but should include at least the mucosal and sub-mucosal tissue at the following locations:

(a) On the lateral aspect of the nasal vault (i.e., the upper third of the nasal cavity), the full length of the superior turbinate and (if present) the supreme turbinate;

(b) On the medial aspect of the nose, the upper third of the perpendicular plate of the ethmoid bone;

(c) The superior third of the rostrum of the right and left side of the sphenoid sinus;

(d) The upper third of the posterior third of the quadrangular nasal cartilage; and (e) The region of the pterygopalatine ganglion (a.k.a. the sphenopalatine ganglion). However, the surgeon may select other locations for placement of therapeutic stem cells (or other injectables) within the nasal cavity depending on the anatomical structure of the nose. For example, the surgeon may alternatively choose to place therapeutic stem cells (or other injectables) at the posterior third of the inferior turbinate.

The above described mucosa locations (regions) within the nasal cavity are chosen for injection of stem cells (or other injectables) because of their rich neurovascular components that have the most potential for the absorption, transportation, and bypassing of the blood brain barrier. These mucosa locations represent the only areas that stem cells, if implanted, might migrate back into the CNS because studies have identified these areas as having adequate (a) blood supply, (b) lymphatic supply, and (c) nerve ending supply. Furthermore, these specific mucosa areas are more prone to accept the implementation of stem cells due to their previously described characteristics than if the stem cells were placed blindly in other mucosa areas of the nose that do not have these characteristics. Moreover, the many mucosal tissue locations available to the surgeon for stem cell injection provide the surgeon ample choices to place stem cells wherever it is easier due to anatomical variations of the nose, e.g., crooked nose, deviated nasal septum, enlarged turbinates, etc.

In one embodiment of the present invention, a predetermined amount (approximately 2 to 3 cubic centimeters) of liquid stem cell solution (e.g., saline or other physical suspension) may be injected into the mucosal tissue at the junction of the upper lip and the nose, while a predetermined amount (approximately another 2 to 3 cubic centimeters) of liquid stem cell solution may be administered to mucosal tissue on each side of the nasal septum. In addition, a predetermined amount (approximately 2 to 3 cubic centimeters) of liquid stem cell solution may be injected into the mucosal tissue of the left superior turbinate and, if present, the left supreme turbinate on one side of the nasal septum, while a predetermined amount (approximately another 2 to 3 cubic centimeters) of liquid stem cell solution may be dispensed into the mucosal tissue of the right superior turbinate and, if present, the right supreme turbinate on the other side of the nasal septum. Similarly, if anatomical variations of the nose require alternative injection sites, a predetermined amount (approximately 2 to 3 cubic centimeters) of liquid stem cell solution may be injected into the mucosal tissue at the posterior third of the left inferior turbinate on the one side of the nasal septum, while a predetermined amount (approximately another 2 to 3 cubic centimeters) of liquid stem cell solution may be dispensed into the mucosal tissue at the posterior third of the right inferior turbinate on the other side of the nasal septum.

While the concentration of stem cells in the liquid stem cell solution (e.g., saline or other physical suspension) may vary, each cubic centimeter of solution usually contains hundreds of thousands to millions of stem cells per cubic centimeter. Thus, it is generally recognized that if approximately 10 cubic centimeters of stem cells is intranasally injected into the mucosal and/or submucosal tissue at the aforementioned regions of the nose, anywhere from 600 million to 1 billion stem cells can be transported into the brain and/or CNS to treat neurodegenerating conditions such as traumatic brain injury, Alzheimer's, Parkinson's, and Huntington's disease to name just a few. However, if a surgeon believes introducing additional stem cells into the brain and/or CNS would be beneficial to treat these conditions as well as other neurological conditions resulting from damage to CNS through aging, disease or injury, simultaneous intravenous (IV) delivery of stem cells in a vein is not precluded.

As discussed, the intranasal stem cell delivery technique of the present invention differs from previous intranasal stem cell delivery approaches in that it provides direct endoscopic visual access to the depth of placement of injectable material (i.e., stem cells) in the mucosa tissue at the aforementioned locations (regions). More importantly, by using the endoscopic intranasal delivery approach to identify the location and depth of placement of the stem cells within the mucosa, i.e., solely within the mucosal and sub-mucosal tissue while avoiding the subperiosteal regions, stem cell survival can be assured and the likelihood that the stem cells will reach the specific sites of damage within the brain and/or CNS is much improved. As mentioned before, this is a critical aspect of the present invention that has not been documented in previous neurotransplanation studies. Thus, the presently described intranasal delivery approach using endoscopy to treat a damaged, degenerating, and injured brain or CNS distinguishes this invention from the previously described intranasal delivery approaches of the prior art.

Furthermore, it has been found that injecting stem cells exclusively into the mucosal area (i.e., the mucosal and sub-mucosal tissue) causes a swelling or ballooning out of the mucosa in this area. Thus, a surgeon having direct endoscopic visual access to the mucosal tissue will immediately know when the depth of placement of injectable material (i.e., stem cells) is in the right place, i.e., the mucosal and/or sub-mucosal tissue, by observing the ballooning out of the mucosa.

Additionally, in the area of the superior turbinate (and, if present, the supreme turbinate), it is important that the injection of the stem cells by way of syringe and needle is applied to the mucosa or sub-mucosa where there is adequate neurovascular component while avoiding at all times blood supply as well as placement of the solution or suspension of stem cells into the avascular subperiosteal or subperichondrial areas. Similarly, in the region of the sphenoid sinus, perpendicular plate of the ethmoid bone and septal cartilage, the injection of stem cells must only be within the depth of the covering mucosa.

Once again, the injection site or sites are chosen by the regions of the nose that are rich in neurovascular components which assures the highest rate of success for delivering stem cells to the brain as well as the CNS. Further, it cannot be overly emphasized that the depth and location of the needle injections are critically important. In the nasal pyramid region, the needle injections should initially be from either right to left or left to right starting at the base of the nasal pyramid beginning at the soft tissue of the nasal ala (wing) under the substance of the nasal philtrum and upper lip. In the lateral wall regions, the needle injections should go under the substance of the nasal ala along the soft tissue at the junction of the nasal maxillary suture line. Needless to say, the surgeon should avoid injections of stem cells into the subperiosteal and subperichondrial regions at all times. Again, the importance of the specific nasal areas chosen for injections of stem cells (or other injectables) is because they are rich in neurovascular components used for absorption and bypass potential of the blood-brain barrier.

Additionally, the technique of the present invention affords the benefit of knowing the amount of stem cells present in every cubic centimeter of solution or suspension to be injected into mucosal tissue of the nose. Thus, from this information, surgeons may determine the amount of stem cells having the potential to reach the human brain and/or CNS for treating neurological deficits of the brain and/or central nervous system. Moreover, this information may one day lead medical personnel to understand the optimum dosage of stem cells for treating specific neurological conditions that can benefit from use of the endoscopic intranasal stem cell delivery approach of the present invention.

Further, a dopamine dot test (DDT) may be used to establish the validity of the above described endoscopic intranasal stem cell delivery approach. Specifically, a preoperative DDT may be compared to a six-month post-operative DDT to determine if there is any improvement in the neurological condition of the patient. In addition, subsequent neurological testing may be performed at regular, predetermined intervals to check if the patient's symptoms have improved.

To summarize, the present invention is directed to a technique for efficiently and effectively delivering stem cells to the brain via an intranasal approach using endoscopy to permit the surgeon to clearly see the injection site that is chosen and the depth of the injection. The stem cell solution or suspension is injected into the mucosal tissue at specific locations where it is documented that there is abundant neurovascular component to ensure maximum absorption and transportation through the blood brain barrier.

Having described preferred embodiments of a new and improved method for intranasal delivery of stem cells to the brain using endoscopy, it is believed that other modifications, variations, and changes will be suggested to those skilled in the art in view of the teachings set forth herein. It is therefore to be understood that all such variations, modifications, and changes are believed to fall within the scope of the invention as defined by the appended claims. Although specific terms are employed herein, they are used in a generic and descriptive sense only and not for purposes of limitation.

What is claimed is:

1. A method for delivery of therapeutic stem cells to a central nervous system of a mammal having a blood-brain barrier and a nose with a nasal cavity, comprising:
    inserting an endoscopic device into said nasal cavity;
    injecting said therapeutic stem cells intranasally into nasal structure within the nasal cavity of the nose using a needle and syringe under endoscopic guidance; and
    enabling said therapeutic stem cells to access the central nervous system by bypassing the blood-brain barrier,
    wherein injecting said therapeutic stem cells comprises:
        injection of said stem cells as a stem cell solution solely within mucosal and sub-mucosal tissue covering said nasal structure,
        causing said mucosal and sub-mucosal tissue to balloon out upon injection of said stem cell solution;
        visually observing the ballooning out of said mucosal and sub-mucosal tissue with said endoscopic device; and
        determining correct depth of placement of the stem cell solution solely within said mucosal and sub-mucosal tissue upon direct visual observation of the ballooning out of said tissue.

2. The method of claim 1, wherein said nasal structure is selected from the group consisting of a superior turbinate, an inferior turbinate, a perpendicular plate of an ethmoid bone, a rostrum of a sphenoid sinus, a quadrangular nasal cartilage, and a pterygonopalatine ganglion.

3. The method of claim 2, wherein injecting said therapeutic stem cells further comprises:
    injection of said stem cells solely in the mucosal and sub-mucosal tissue within an upper third of the nasal cavity along the full length of the superior turbinate and, if present, the supreme turbinate.

4. The method of claim 2, wherein injecting said therapeutic stem cells further comprises:
    injection of said stem cells solely in the mucosal and sub-mucosal tissue along an upper third of the perpendicular plate of the ethmoid bone.

5. The method of claim 2, wherein injecting said therapeutic stem cells further comprises:
    injection of said stem cells solely in the mucosal and sub-mucosal tissue along a superior third of the rostrum of the sphenoid sinus on its right and left side.

6. The method of claim 2, wherein injecting said therapeutic stem cells further comprises:
    injection of said stem cells solely in the mucosal and sub-mucosal tissue along an upper third of a posterior third of the quadrangular nasal cartilage.

7. The method of claim 2, wherein injecting said therapeutic stem cells further comprises:
    injection of said stem cells solely in the mucosal and sub-mucosal tissue in a region of the pterygonopalatine ganglion.

8. The method of claim 2, wherein injecting said therapeutic stem cells further comprises:
    injecting said stem cells solely in the mucosal and sub-mucosal tissue at a posterior third of the inferior turbinate.

9. The method of claim 1, wherein injecting said therapeutic stem cells includes injecting 2 to 3 cubic millimeters of said stem cell solution.

10. The method of claim 1, wherein the mammal is a human patient, the method further comprising:
    performing pre-operative and post-operative dopamine dot tests on the human patient, and comparing the pre-operative and a post-operative tests to determine whether the injection of said stem cell solution solely improved a neurodegenerative condition affecting the human patient.

11. A method for delivery of therapeutic stem cells to a central nervous system of a mammal having a blood-brain barrier and a nose with a nasal cavity, comprising:
  inserting an endoscopic device into said nasal cavity;
  injecting said therapeutic stem cells intranasally into nasal structure within the nasal cavity of the nose using a needle and syringe under endoscopic guidance; and
  enabling said therapeutic stem cells to access the central nervous system by bypassing the blood-brain barrier,
  wherein injecting said therapeutic stem cells comprises injection of said stem cells as a stem cell solution solely within mucosal and sub-mucosal tissue covering said nasal structure,
  wherein the mammal is a human patient, and
  wherein the method further comprises:
    performing pre-operative and a post-operative dopamine dot tests on the human patient, and
    comparing the pre-operative and a post-operative tests to determine whether the injection of said stem cell solution solely improved a neurodegenerative condition affecting the human patient.

* * * * *